United States Patent [19]

Fung et al.

[11] Patent Number: 5,593,826
[45] Date of Patent: Jan. 14, 1997

[54] ENZYMATIC LIGATION OF 3'AMINO-SUBSTITUTED OLIGONUCLEOTIDES

[75] Inventors: Steven Fung, Palo Alto; Sergei M. Gryaznov, San Mateo, both of Calif.

[73] Assignee: Perkin-Elmer Corporation, Applied Biosystems, Inc., Foster City, Calif.

[21] Appl. No.: 48,975

[22] Filed: Apr. 16, 1993

Related U.S. Application Data

[63] Continuation-in-part of Ser. No. 38,663, Mar. 22, 1993, abandoned.

[51] Int. Cl.$^6$ .............................. C12Q 1/68; C07H 21/04
[52] U.S. Cl. ................................... 435/6; 536/24.3
[58] Field of Search .................. 435/6; 536/24.3

[56] References Cited

U.S. PATENT DOCUMENTS 4,883,750  11/1989  Whiteley et al. .............................. 435/6
4,988,617   1/1991  Landegren et al. .......................... 435/6

FOREIGN PATENT DOCUMENTS

PCT/US89/
01471  10/1989  WIPO .

OTHER PUBLICATIONS

Iovannisci et al, Clinical Chemistry, 37:1522–1523 (1991).
Nickerson et al, Proc. Natl. Acad. Sci., 87:8923–8927 (1990).
Barany, PCR Methods and Applications, 1:5–16 (1991).
Wu et al, Genomics, 4:560–569 (1989).
Barany, Proc. Natl. Acad. Sci., 88:189–193 (1991).
Zielinski et al, Nucleic Acids Research, 15:1699–1715 (1987).
Zielinski et al, Nucleic Acids Research, 13:2469–2484 (1985).
Glinski et al, Chemical Communications, 1970:915–916 (1970).
Gryaznov et al, Nucleic Acids Research, 20:3403–3409 (1992).
ehman, DNA igase: Structure, Mechanism, and Function, Science, 186:790–797 (1974).
Engler and Richardson, DNA igases, The Enzymes, 15:3–29 (1982).

*Primary Examiner*—Nancy T. Vogel
*Attorney, Agent, or Firm*—Wilson Sonsini Goodrich & Rosati

[57] ABSTRACT

Method and kits are provided for detecting one or more target nucleic acids. A first oligonucleotide having a 3' amino group and a second oligonucleotide having a 5' phosphate group are annealed to a contiguous complementary region of a target nucleic acid. Whenever the 3' terminal nucleotides of the first oligonucleotide and the 5' nucleotides of the second oligonucleotide are complementary to the opposing nucleotides on the target nucleic acid, a nucleic acid ligase ligates the first and second oligonucleotides via the formation of a phosphoramidate linkage. The presence of the target nucleic acid is determined by detection of the ligated first and second oligonucleotides.

18 Claims, No Drawings

ENZYMATIC LIGATION OF 3'AMINO-SUBSTITUTED OLIGONUCLEOTIDES

This is a continuation-in-part of application Ser. No. 08/038,663 filed 22 March 1993, now abandoned.

The invention relates to a method for enzymatic ligation of an oligonucleotide having 3'-amino group with a 5'-phosphorylated oligonucleotide to form a conjugate having a phosphoramidate linkage. More particularly, the invention relates to improvements in ligation-based assays for detecting specific nucleotide sequences.

BACKGROUND

Nucleic acid sequence analysis is becoming increasingly important in many research, medical, and industrial fields, e.g. Caskey, Science 236:1223–1228 (1987); Landegren et al, Science, 242:229–237 (1988); and Arnheim et al, Ann. Rev. Biochem., 61:131–156 (1992). In particular, ligation-based techniques, such as oligonucleotide ligation assay (OLA), ligation chain reaction (LCR), ligation amplification reaction (LAR), and the like, form an important family of sequence analysis tools, e.g. Barany, PCR Methods and Applications 1:5–16 (1991); Landegren et al, U.S. Pat. No. 4,988,617; Landegren et al, Science 241: 1077–1080 (1988); Backman et al, European patent publication 0439182A2; Whiteley et al, U.S. Pat. No. 4,883,750; Yu and Wallace, Genomics 4:560–569 (1989); Nickerson et al, Proc. Natl. Acad. Sci. 87:8923–8927 (1990); and the like.

Ligation-based techniques rely on oligonucleotides annealing to contiguous regions of a target sequence. If there is perfect complementarity between the target sequence and the oligonucleotides at the junction between the oligonucleotides, then ligation can be effected. If the terminal nucleotide of either oligonucleotide is not complementary with its corresponding nucleotide on the target sequence at the junction, then ligation cannot be effected. A key feature of ligation-based assays is the ability of the ligation reaction, whether chemical or enzymatic in nature, to distinguish between mispairing at the junction and perfect complementarity at the junction. However, even if the terminal nucleotides are complementary with their corresponding target nucleotides, ligation can still fail if one of the terminal nucleotides has a substantial residence time in a non-annealed equilibrium state, for example, as may occur with AT-rich termini or ligation is attempted at high temperature. The result is a loss of sensitivity in the assay employing the ligation.

The sensitivity of ligation-based techniques for analyzing nucleotide sequences would be substantially increased with the availability of a method for enhancing the stability of oligonucleotides hybridized to a complementary target sequence.

SUMMARY OF THE INVENTION

The invention relates to a method and kits for enzymatic ligation of an oligonucleotide having a 3'-amino group with a 5'-phosphorylated oligonucleotide to form a conjugate having a phosphoramidate linkage. An important aspect of the invention is the detection of one or more target nucleic acids by a ligation-based assay employing a first oligonucleotide having a 3' amino group and a second oligonucleotide having a 5' monophosphate group. In such assays, whenever a target nucleic acid is present in a sample, the first and second oligonucleotides are annealed to contiguous complementary sequence regions on the target nucleic acid such that the 3' amino group of the first oligonucleotide abuts the 5' monophosphate group of the second oligonucleotide thereby permitting first oligonucleotide to be covalently joined to the second oligonucleotide by a ligase. The ligation results in the formation of a phosphoramidate linkage between the first and second oligonucleotides. In the absence of a perfectly complementary target nucleic acid, substantially no ligation takes place either because one or both of the oligonucleotides fails to anneal to the target nucleic acid, or because one or more of the 3' terminal nucleotides of the first oligonucleotide, or one or more of the 5' terminal nucleotides of the second oligonucleotide are not complementary to their respective opposing nucleotides on the target sequence. Usually, the 3' and 5' terminal nucleotides are the first and second nucleotides from the 3° end of the first oligonucleotide and the first and second nucleotides from the 5' end of the second oligonucleotide, respectively. These four nucleotides will sometimes be referred to herein as the 3' terminal nucleotide, the 3' penultimate nucleotide, the 5' terminal nucleotide, and the 5' penultimate nucleotide, respectively.

In one aspect, the method provides a means of detecting one or more target polynucleotides, either directly or after amplification by other techniques, e.g. as described by Landegren et al, U.S. Pat. No. 4,988,617; Mullis U.S. Pat. No. 4,683,202; Mullis et al U.S. Pat. No. 4,965,188; and the like. In this aspect, the method employs two oligonucleotides for each contiguous complementary region.

In another aspect, the method provides a means of amplifying and detecting one or more target polynucleotides. In this aspect, it is understood that a target polynucleotide is a double stranded polynucleotide and that a pair of first oligonucleotides and a pair of second oligonucleotides are employed in amplifying the target polynucleotide in accordance with the principles described by Landegren et al, U.S. Pat. No. 4,988,617.

An important feature of the invention is the discovery that ligases are capable of catalyzing the reaction of a 3' amino and a 5' monophosphate to form a phosphoramidate linkage. This permits the use of oligonucleotides having a 3' amino in ligation-based assays. This class of oligonucleotides forms more stable hybrids with complementary sequences as compared to their 3' hydroxyl counterparts. The increased stability results in a more sensitive detection of target nucleic acids in ligation-based assays because the stringency of the annealing conditions can be increased, thereby reducing background signals.

DEFINITIONS

"Ligation-based assay" means any assay that employs the ligation, or covalent joining, of two or more oligonucleotides as a means of detecting the presence of the complementary nucleotide sequences of the ligated oligonucleotides. In particular, ligation-based assays include oligonucleotide ligation assays (OLA), U.S. Pat. No. 4,883,750; ligase chain reaction (LCR) assays, e.g. Barany, Proc. Natl. Acad. Sci., 88:189–193 (1991); ligase amplification reaction (LAR) assays, e.g. Wu and Wallace, Genomics, 4:560–569 (1989); polymerase-ligase chain reaction (PLCR) assays, e.g. Backman et al, European patent publ. 0 439 182 A2 (1991); and like assays.

"Contiguous complementary region" in reference to target nucleic acids means an uninterrupted sequence of nucleotides in a target nucleic acid to which oligonucleotides of the invention are directed for hybridization and which permits such oligonucleotides to be covalently joined by a ligase, either alone or in conjunction with a polymerase.

"Abut" in reference to the first and second oligonucleotides of the invention means that the 3' terminus of the first oligonucleotide is sufficiently close to the 5' terminus of the second oligonucleotide, and in the proper orientation with respect to the 5' terminus, so that a ligase can covalently join the two oligonucleotides by way of a phosphoramidate linkage.

"Phosphoramidate linkage" in reference to ligation means the formation of a linkage between the 3' terminal nucleoside of the first oligonucleotide and the 5' terminal nucleoside of the second oligonucleotide, which linkage is an analog of the natural phosphodiester linkage such that a bridging oxygen (—O—) is replaced with an amino group (—NR—), wherein R is selected from the group consisting of hydrogen and alkyl having from one to three carbon atoms. Preferably, R is selected from the group consisting of hydrogen and methyl. Most preferably, R is hydrogen.

"Enzymatically ligating" in reference to the first and second oligonucleotides means the covalent joining of the oligonucletides in a method which includes a reaction catalyzed by a ligase. It is appreciated that the term includes methods which further include the use of polymerases which extend the first oligonucleotide to bring it into an abutting position with the second oligonucleotide.

"Target nucleic acid" means any DNA or RNA for which first and second oligonucleotides could be prepared and hybridized to; preferably, a target nucleic acid is a single-stranded polydeoxyribonucleic acid.

"Anneal" in reference to the first and second oligonucleotides and a contiguous complementary region of a target nucleic acid means hybridization of, or the formation of duplexes between, the first and second oligonucleotides and a contiguous complementary region.

"Opposing nucleotide" in reference to the 3' terminal nucleotides of the first oligonucleotide and the 5' terminal nucleotides of the second oligonucleotide means the nucleotides of the contiguous complementary region that would undergo Watson-Crick base pairing with the 3' terminal nucleotides of the first oligonucleotide and the 5' terminal nucleotides of the second oligonucleotide, respectively, provided such nucleotides were complementary to the 3' terminal nucleotides and 5' terminal nucleotides.

DETAILED DESCRIPTION OF THE INVENTION

The invention is directed to an improvement in ligation-base assays, particularly those which employ ligases that require double-stranded substrates. A key feature of the invention is the use of a first oligonucleotide having a 3' amino group which permits the formation of a more stable duplex with contiguous complementary regions of a target nucleic acids whenever the 3' terminal nucleotide and its opposing nucleotide are complementary. As with other ligation-based assays, detection of a target nucleic acid is based on the covalent joining of the first oligonucleotide with a second oligonucleotide, which joining is dependent on the 3' terminal nucleotides of the first oligonucleotide and the 5' terminal nucleotides of the second oligonucleotide being complementary to their respective opposing nucleotides on the target sequence.

Preferably, first oligonucleotides are synthesized on a solid phase support as described by Gryaznov and Letsinger, Nucleic Acids Research, 20:3403–3409 (1992), which is incorporated by reference. Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropyl-ethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18–20 hours at room temperature. 5'-amino-5',3'-deoxynucleosides may be synthesized in accordance with Glinski et al, J. Chem. Soc. Chem. Comm., 915–916 (1970); Miller et al, J. Org. Chem. 29:1772 (1964); Zielinki and Orgel, Nucleic Acids Research, 13:2469–2484 (1985) and 15:1699–1715 (1987); Ozols et al, Synthesis, 7:557–559 (1980); and Azhayev et al, Nucleic Acids Research, 6:625–643 (1979); which references are incorporated by reference.

A first oligonucleotide may also be formed on a target polynucleotide by annealing a first oligonucleotide precursor to a contiguous complementary region then extending the precursor with a nucleic acid polymerase in the presence of 3'-aminonucleoside triphosphates so that the final product abuts the second oligonucleotide. 3'-aminonucleoside triphosphates are disclosed in Azhayev et al (cited above). In this embodiment, it is understood that the 3' terminal nucleotide is with respect to the first oligonucleotide precursor. If the 3' terminal nucleotides are not complementary to their opposing nucleotides, then either the first oligonucleotide precursor will not hybridize or it will not be extended by a nucleic acid polymerase.

Second oligonucleotides are synthesized by conventional means, e.g. via phosphoramidite chemistry on a commercial DNA synthesizer. A 5' monophosphate can be attached to a second oligonucleotide either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lett., 27:4705 (1986), and reagents are commercially available, e.g. 5'Phosphate-ON™ from Clontech Laboratories (Palo Alto, Calif.).

The first and second oligonucletides may contain one or more nucleoside analogs, which may be incorporated for a variety of reasons, including to permit a single oligonucleotide to bind to different target sequences in different samples, to modify the binding characteristics of an oligonucleotide, or the like, e.g. as disclosed in Macevicz, U.S. Pat. No. 5,002,867.

The first and second oligonucleotide may have the same or different lengths. The length of the first oligonucleotide is selected so as to maximize specificity. Usually, it is as short as possible consistent with the operation of the ligase and specific binding of the first oligonucleotide to the target nucleic acid under a given set of ligation reaction condition. Preferably, the first oligonucleotide is in the range of 10–20 nucleotides in length. More preferably, the first oligonucleotide is in the range of 12–20 nucleotides in length. The second oligonucleotide is at least long enough to confer specificity and to permit a ligase to operate after annealing takes place, but it is not so long as to be inconvenient to synthesize. Preferably, the second oligonucleotide is in the range of 10–30 nucleotides in length. More preferably, the second oligonucleotide is in the range of 12–20 nucleotides in length.

Several ligases have been described and are commercially available that can be used in accordance with the invention, e.g. Lehman, Science: 186:790–797 (1974); Kornberg and Baker, DNA Replication, pages 307–315 (Freeman, New York, 1992); Higgins and Cozzarelli, Methods in Enzymol. 68:50–71 (1979); Barker et al, Nucleic Acids Research, 13:8323–8337 (1985); Armstrong et al, Nucleic Acids Research, 11:7145–7156 (1983); Rabin et al, J. Biol. Chem. 261:10637–10647 (1986); Takahashi et al, J. Biol. Chem. 259:10041–10047 (1983); Barany et al, PCT application No. PCT/US91/02968; and like references. Conditions for using ligases are generally well known in the art and are described in references such as Sambrook et al (cited above); Barany, PCR Methods and Applications, 1:5–16 (1991); Nickerson et al, Proc. Natl. Acad. Sci., 87:8923–8927 (1990); Landegren et al, U.S. Pat. No. 4,988,617 (which patent is incorporated by reference); and the like. Usually, target polynucleotides would be denatured DNA at a concentration of between about 1 μg/mL to about 100 μg/mL in a ligation buffer solution. The ligation buffer solution is an aqueous solution at a pH that ensures the selected ligase will be active; typically, this is a pH of between about 7–9. Preferably, the pH is maintained by Tris-HCl at a concentration of between about 5 mM to 50 mM. The ligation buffer solution may include one or more nuclease inhibitors, usually calcium ion chelators, such as EDTA. Typically, EDTA is included at a concentration of between about 0.1 to 10 μM. The ligation buffer solution includes whatever cofactors are required for the selected ligase to be active. Usually, this is a divalent magnesium ion at a concentration of between about 0.2 mM to 20 mM, typically provided as a chloride salt. For $E.\ coli$ DNA ligase, NAD is required as a cofactor and for T4 DNA ligase ATP is required as a cofactor. The ligase buffer solution also includes a reducing agent, such as dithiothreitol or dithioerythritol, typically at a concentration of between about 0.1 mM to about 10 mM. Optionally, the ligase buffer may contain agents to reduce nonspecific binding of the oligonucleotides and polynucleotides. Exemplary, agents include salmon sperm DNA, herring sperm DNA, serum albumin, Denhardt's solution, and the like.

Preferably, ligation conditions are adjusted so that ligation will occur if the first and second oligonucleotides form perfectly matched duplexes with the bases of the contiguous complementary region of the target sequence. However, it is understood that it may be advantageous to permit non-pairing nucleotides on the 5' end of the first oligonucleotide and the 3' end of the second oligonucleotide in some embodiments to aid in detection or to reduce blunt-end ligation, e.g. as taught by Barany, Proc. Natl. Acad. Sci. (cited above). Important parameters in the ligation reaction include temperature, salt concentration, presence or absence and concentration of denaturants such as formamide, concentration of the first and second oligonucleotides, type of ligase employed, and the like. Guidance in selecting hybridization conditions for the reaction can be found in numerous references, e.g. Wetmur, Critical Reviews in Biochemistry and Molecular Biology, 26:227–259 (1991); Dove and Davidson, J. Mol. Biol. 5:467–478 (1962); Hutton, Nucleic Acids Research, 10: 3537–3555 (1977); Breslauer et al, Proc. Natl. Acad. Sci. 83:3746–3750 (1986); Innis et al, editors, PCR Protocols (Academic Press, New York, 1990); and the like. Preferably, ligation occurs under stringent hybridization conditions to ensure that only perfectly matched oligonucleotides hybridize. Typically, stringency is controlled by adjusting the temperature at which hybridization occurs while holding salt concentration at some constant value, e.g. 100 mM NaCl, or the equivalent. It is understood that other relevant factors include the particular sequence of the first and second oligonucleotides, the length of the first and second oligonucleotide, the heat lability of the ligase selected, and the like. Preferably, the ligation reaction is carried out at a temperature close to the melting temperature of the hybridized oligonucleotides in the ligation buffer solution. More preferably, the ligation reaction is carried out at a temperature within 10° C. of the melting temperature of the hybridized oligonucleotides in the ligation buffer solution. Most preferably, the ligation reaction is carried out at a temperature in the range of 0°–5° C. below the melting temperature of the hybridized oligonucleotides in the ligation buffer solution.

After the ligation reaction is completed or quenched, the ligated product of the first and second oligonucleotides, if one is present, is usually separated from the reaction mixture for detection, e.g. via electrophoresis, fluorescent analysis, or the like.

The method of the invention may be applied to detect target polynucleotides from diverse origins, e.g. human diagnostic samples, plant samples, samples from microorganism cultures, and the like. Nucleic acid samples for application of the method of the invention are prepared by standard techniques, e.g. Kawasaki, chapter 18, in Innis et al (cited above). In fetal testing, samples can be obtained by amniocentesis using the technique disclosed by Barter, Am. J. Obstet. Gynecol., 99: 795–805, or samples can be obtained from maternal peripheral blood using fluorescence-activated cell sorting as described by Iverson et al, Prenatal Diagnosis, 9:31–48 (1981); and the like. Other tissues and sample sources may require different nucleic isolation procedures. Guidance for specific protocols can be found in standard texts, such as Davis et al, Basic Methods in Molecular Biology (Elsevier, N.Y., 1986). In some embodiments, a target polynucleotide may be formed by reverse transcription of one or more RNAs of interest using well known techniques, e.g. Ausubel et al, Current Protocols in Molecular Biology, pages 3.7.1–3.7.3 (Wiley-lnterscience, New York, 1987). Once isolated, DNA target polynucleotides are rendered single stranded by well known techniques, e.g. heating in the ligation buffer solution to melting temperature, usually between about 80° C. and 100° C.

First and second oligonucleotides ligated in accordance with the invention can be detected by a variety of ways, e.g. as disclosed by Matthews et al, Anal. Biochem. 169:1–25 (1988). In one preferred embodiment, the first and/or second oligonucleotides are modified by covalently attaching chemical groups that modify the electrophoretic mobility of the ligated product of the first and second oligonucleotides, e.g. as disclosed by Kornher et al, Nucleic Acids Research, 17:7779–7784 (1989); Livak et al, Nucleic Acids Research, 20:4831–4837 (1992); Jaschke et al, Tetrahedron Letters, 34: 301–304 (1993); and the like. In this way, sets of similarly sized first and second oligonucleotides can be employed to detect the presence of multiple target polynucleotides. Covalent modifications are selected that change the electrophoretic mobility of the ligation products to different degrees, thereby permitting detection of multiple target polynucleotides by a pattern of bands after electrophoretic separation, e.g. as taught by Mayrand et al, Clinical Chemistry, 36:2063–2071 (1990).

First and/or second oligonucleotides of the invention may be radioactively labeled with $^{32}P$ using standard protocols for electrophoretic detection or detection by other means, e.g. Maniatis et al, *Molecular Cloning: A Laboratory Manual* (Cold Spring Harbor Laboratory, New York, 1982); *Current Protocols in Molecular Biology*, Unit 6.4 (John Wiley & Sons, New York, 1987); or Maxim and Gilbert, *Meth. Enzymol.*, Vol. 65, pgs. 499–560 (1980).

Preferably, first and/or second oligonucleotides are labeled fluorescently by linking a fluorescent molecule to one or both of the oligonucleotides, e.g. as taught by Fung et al, U.S. Pat. Nos. 4,757,141; 4,855,225; or the like. Preferably, different ligated first and second oligonucleotides are labeled with different fluorescent labels. Guidance for selecting appropriate fluorescent labels can be found in Smith et al, Methods in Enzymology, Vol. 155, pgs. 260–301 (1987); Karger et al., Nucleic Acids Research, Vol. 19, pgs. 4955–4962 (1991); Haugland, Handbook of Fluorescent Probes and Research Chemicals (Molecular Probes, Inc., Eugene, Oreg., 1989), and the like. Preferred fluorescent labels include, fluorescein and derivatives thereof, such as disclosed by Khanna et al, U.S. Pat. No. 4,318,846 and/or Menchen et al, U.S. Pat. No. 5,188,934, tetramethylrhodamine, rhodamine X, Texas Red, and the like. Most preferably, when a plurality of fluorescent dyes are employed they are spectrally resolvable, as taught by Fung et al (cited above). Briefly, as used herein "spectrally resolvable" fluorescent dyes are those with quantum yields, emission bandwidths, and emission maxima that permit electrophoretically separated polynucleotides labeled thereby to be readily detected despite substantial overlap of the concentration bands of the separated polynucleotides.

In some embodiments, detection of the ligated product of the first and second oligonucleotides can be improved by modifying one of the oligonucleotides to include a "hook" moiety, e.g. as defined by Whiteley et al (cited above). Exemplary "hooks" include biotin, hapten-modified nucleotides, and the like, which can be isolated via avidin or streptavidin coated supports or microparticles, or via antibodies, respectively.

In one embodiment, kits of the invention comprise one or more first and second oligonucleotides pairs, a nucleic acid ligase, and a ligase buffer solution. The one or more first and second oligonucleotide pairs may be provided separately or as a mixture dissolved in an appropriate solution, e.g. TE (10 mM Tris-HCl (pH 8.0) and 1 mM EDTA (pH 8.0)). The ligase buffer solution will typically be optimized for both the nucleic acid ligase selected (as discussed above) and the particular first and second oligonucleotides employed. Usually, a kit will also include at least one pair control oligonucleotides, i.e. first and second oligonucleotides specific for a known target polynucleotide in a sample to confirm that a ligation reaction has taken place successfully even though a target polynucleotide of interest is not detected.

EXAMPLE 1

Ligation of first and second oligonucleotides after annealing to a target polynucleotide A first oligonucleotide was prepared in accordance with Gryaznov and Letsinger (cited above) having the sequence 5'-NH$_2$-TTT TTT TTT T-NH$_2$-3' (SEQ ID NO:1). A second oligonucleotide was prepared on a controlled pore glass support with 3'-amine-ON™ CPG (Clontech, Palo Alto, Calif.) and 5'-phosphate-ON™ (Clontech, Palo Alto, Calif.) using published manufacturers' and/or published protocols, e.g. Applied Biosystems, Inc. Model 392 and 394 DNA/RNA Synthesizers Users Manual (Foster City, Calif.); Caruthers et al, J. Am. Chem. Soc. 113:6324 (1991); Connell et al, Biotechniques, 5:342 (1987); and the like. After cleavage from the CPG support the free 3° amine was reacted with an N-hydroxysuccinimide ester of the carboxyfluorescein dye JOE (Applied Biosystems, Inc., Foster City, Calif.) to form a fluorescently labeled second oligonucleotide of the following sequence: 5'-(phosphate)-TTG GTG TTT CCT ATG ATG AAT ATA G-(JOE)-3'(SEQ ID NO:2). The following target polynucleotide was prepared using published methods: 5'-CTA TAT TCA TCA TAG GAA ACA CCA AAA AAA AAA AA-3'(SEQ ID NO:3).

The first and second oligonucleotides were annealed to the target polynucleotide and ligated with T4 DNA ligase (400 U/μL, New England Biolabs, Inc., Beverly, Mass.). 10X of the T4 ligase buffer solution consisted of 500 mM Tris-HCl, pH 7.5, 100 mM MgCl$_2$, 100 mM dithiothreitol (DTT), 10 mM ATP, 250 μg/mL bovine serum albumin (BSA). In a Gene-Amp™ reaction tube (Perkin-Elmer Cetus, Norwalk, Conn.), the ligation reaction mixture contained the first oligonucleotide (10 μL at 500 nM in water), the second oligonucleotide (10 μL at 50 nM in water), the target polynucleotide (10 μL at 50 nM in water), T4 DNA ligase 80 units, 10 μL 10X ligation buffer, 4 mg herring sperm DNA in 10 μL water, and 50 μL water. The reaction mixture was overlayed with 60 μL of mineral oil and placed in a Perkin-Elmer Cetus DNA thermal cycler where it was consecutively held at 15° C., 25° C., 35° C., 45° C., and 55° C. for 30 minutes at each temperature. The aqueous layer was precipitated with 3 M sodium acetate (10 μL) and ethanol (250 μL), after which it was put on dry ice (15 min), centrifuged (15 min), decanted, rinsed with 70% ethanol (200 μL), centrifuged (15 min), decanted, and dried in a Savant. One fortieth of the sample in formamide with 50 mM EDTA (5 μL) was analyzed on an Applied Biosystems, Inc. (Foster City, Calif.) model 373A DNA sequencer using a 6% polyacrylamide gel. The resulting electropherogram indicated substantial presence of the phosphoramidate ligation product. In a control experiment run identically to that above, with the exception that no target polynucleotide was included in the ligation reaction mixture, no ligation product was observed. In another experiment identical to the above with the exception that the ligation reaction was carried out at 25° C. for 2 hours, ligation product was also observed, whereas in the control reaction without target polynucleotide no ligation product was observed.

EXAMPLE 2

Detection of the sickle cell mutation of the β-globin gene

Cells isolated from peripheral blood of an individual homozygous for the β$_s$ genotype are lysed with 20 μL of 0.1 M KOH and 0.1% Triton X-100 at 65° C. for 20 min and neutralized with 20 mL of 0.1 M HCl and 0.1% Triton X-100. Genomic DNA is isolated by a standard phenol/chloroform extraction procedure followed by ethanol precipitation. The β-globin gene is amplified by polymerase chain reaction (PCR) with primers 5'-CAACTTCATC-CACGTTCACCTTGCC (SEQ ID NO:4) and 5'-AGGGCAGGAGCCAGGGCTGGG (SEQ ID NO:5) using standard protocols. Briefly, in a Gene-Amp™ reaction tube, PCR reagents (5 μL containing 20 mM Tris-HCl (pH 8.3), 100 mM KCl, 3 mM MgCl$_2$, 20 ng/mL bovine serum albumin, the four deoxynucleotide triphosphates each at 400 μM, primers each at 0.5 μM, 0.1% Triton X-100, and 0.05 unit of Taq DNA polymerase), genomic DNA (5μL at 2 ng/μL in sterile distilled water containing 0.1% Triton X-100), and 70 μL mineral oil. The DNA is denatured by incubation at 93° C. for 4 minutes and amplified by 40 cycles of 93° C. for 30 sec, 61° C. for 45 sec, and 72° C. for 90 sec. Amplified DNA is denatured with 45 μL of 0.25 m NaOH containing 0.1% Triton X-100. The first and second oligonucleotides prepared in accordance with the invention (5'-ATGGTGCACCTGACTCCTGT-NH$_2$ (SEQ ID NO:6)and 5'-(phosphate)-GGAGAAGTCTGCCGT-TACTG-(JOE)) (SEQ ID NO:7) (200 fmol each) in 10 μL of 50% formamide and 2X ligase buffer solution (100 mM Tris-HCl, pH 7.5, 20 mM MgCl$_2$, 2 mM spermidine, 2 mM ATP, 10 mM DTT) are added to a Gene-Amp™ reaction tube, or the like. The DNA sample is neutralized with 45 μL of 0.25 M HCl and added to the first and second oligonucleotides in the above reaction mixture, after which the reaction mixture is covered with 70 μL of mineral oil. After the amplified DNA is denatured at 93° C. for 2 min and cooled, 5 μL of T4 DNA ligase (5 units/mL) is added in 1X ligase buffer solution. The ligase reaction is allowed to proceed at room temperature for 2 hours, after which it is cooled to 4° C. The reaction mixture is then precipitated with ethanol, after which the precipitate is redissolved in 5 μL of formamide/EDTA, 50 mmol/L (4/1 by volume). After denaturation at 93° C. for 2 minutes, the DNA components of the solution are loaded onto a gel of a DNA sequencer (Applied Biosystems, model 373A) with a 6% acrylamide gel in 8 M urea, Tris-borate buffer (per liter: 89 mmol Tris-HCl, 89 mmol boric acid, and 2 mmol EDTA, pH 8.3). Electrophoresis is carried out for 2 hours at 1500 V. Analysis of the DNA components shows the presence of the JOE-labeled ligation product and the absence of any appreciable signal from unligated first oligonucleotide.

---

We claim:

1. In a ligation-based assay for detecting one or more target nucleic acids wherein a first oligonucleotide having a 3' terminus and a second oligonucleotide having a 5' terminus are annealed to contiguous complementary regions of a target nucleic acid such that the 3' terminus of the first oligonucleotide is made to abut the 5' terminus of the second oligonucleotide, an improvement comprising:

providing a first oligonucleotide having a 3' amino group at the 3' terminus and a second oligonucleotide having a 5' monophosphate group at the 5' terminus; and enzymatically ligating the first and second oligonucleotides through the formation of a phosphoramidate bond when both the first and second oligonucleotides are annealed to a target nucleic acid.

2. The method of claim 1 wherein said 3' amino group is defined by a formula —NRH, wherein N is nitrogen, H is hydrogen, and R is selected from the group consisting of hydrogen and alkyl having from 1 to 3 carbon atoms.

3. The method of claim 2 wherein R is hydrogen.

4. The method of claim 3 wherein said step of enzymatically ligating is carried out with T4 DNA ligase.

5. A method for detecting a target nucleic acid in a sample comprising:

contacting the sample under conditions favorable for annealing with a first oligonucleotide having a 3' terminus with an amino group at the 3' terminus and a second oligonucleotide having a 5' terminus with a monophosphate group at the 5' terminus, the first and second oligonucleotides being complementary to contiguous regions of the target nucleic acid such that the 3' terminus of the first oligonucleotide abuts the 5' terminus of the second oligonucleotide when both the first and second oligonucleotides are annealed to the target nucleic acid;

enzymatically ligating the 3' terminus of the first oligonucleotide and the 5' terminus of the second oligonucleotide through the formation of a phosphoramidate bond when both the first and second oligonucleotides are annealed to the target nucleic acid; and detecting any ligated first and second oligonucleotides.

6. The method according to claim 5 wherein the 3' amino group is defined by a formula —NRH, wherein N is nitrogen, H is hydrogen, and R is selected from the group consisting of hydrogen and a $C_{1-3}$ alkyl.

7. The method according to claim 6 wherein R is hydrogen.

8. The method according to claim 5 wherein enzymatic ligation is performed using a T4 DNA ligase.

9. A kit for detecting a target nucleic acid by a ligation-based assay comprising:

a first oligonucleotide having a 3' terminus with an amino group at the 3' terminus; and a second oligonucleotide having a 5' terminus with a monophosphate group at the 5' terminus, the first and second oligonucleotides being complementary to contiguous regions of the target nucleic acid such that the 3' terminus of the first oligonucleotide abuts the 5' terminus of the second oligonucleotide when the first and second oligonucleotides are annealed to the target nucleic acid.

10. The kit according to claim 9 wherein the kit further includes a nucleic acid ligase capable of forming a phosphoramidate bond by linking the 3' terminus of the first oligonucleotide with the 5' terminus of the second oligonucleotide when the first and second oligonucleotides are annealed to the target nucleic acid.

11. The kit according to claim 10 wherein the ligase is a T4 DNA ligase.

12. The kit according to claim 9 wherein the 3' amino group is defined by a formula —NRH, wherein N is nitrogen, H is hydrogen, and R is selected from the group consisting of hydrogen and a $C_{1-3}$ alkyl.

13. The kit according to claim 12 wherein R is hydrogen.

14. A method for detecting a target nucleic acid in a sample of nucleic acids comprising:

amplifying the target nucleic acid;

contacting the sample of nucleic acids under conditions favorable for annealing with a first oligonucleotide having a 3' terminus with an amino group at the 3' terminus and a second oligonucleotide having a 5' terminus with a monophosphate group at the 5' terminus, the first and second oligonucleotides being complementary to contiguous regions of the target nucleic acid such that the 3' terminus of the first oligonucleotide abuts the 5' terminus of the second oligonucleotide when both the first and second oligonucleotides are annealed to the target nucleic acid;

enzymatically ligating the 3' terminus of the first oligonucleotide to the 5' terminus of the second oligonucleotide through the formation of a phosphoramidate bond when both the first and second oligonucleotides are annealed to the target nucleic acid; and detecting any ligated first and second oligonucleotides.

15. The method according to claim 14, further including the step of isolating the ligated first and second oligonucleotides.

16. The method according to claim 14 wherein the 3' amino group is defined by a formula —NRH, wherein N is nitrogen, H is hydrogen, and R is selected from the group consisting of hydrogen and a $C_{1-3}$ alkyl.

17. The method according to claim 16 wherein R is hydrogen.

18. The method according to claim 14 wherein enzymatic ligation is performed using a T4 DNA ligase.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 10 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TTTTTTTTTT      10

( 2 ) INFORMATION FOR SEQ ID NO: 2:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TTGGTGTTTC CTATGATGAA TATAG      25

( 2 ) INFORMATION FOR SEQ ID NO: 3:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CTATATTCAT CATAGGAAAC ACCAAAAAAA AAAAA      35

( 2 ) INFORMATION FOR SEQ ID NO: 4:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CAACTTCATC CACCTTCACC TTGCC      25

( 2 ) INFORMATION FOR SEQ ID NO: 5:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

AGGGCAGGAG CCAGGGCTGG G                          21

( 2 ) INFORMATION FOR SEQ ID NO: 6:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

ATGGTGCACC TGACTCCTGT                           20

( 2 ) INFORMATION FOR SEQ ID NO: 7:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GGAGAAGTCT GCCCTTACTG                           20